(12) United States Patent  
Simon et al.

(10) Patent No.: US 7,706,047 B2
(45) Date of Patent: Apr. 27, 2010

(54) ACOUSTO-OPTICAL LASER SCANNER AND UV LASER ANALYZER OF MICRO-OBJECTS BASED ON IT

(76) Inventors: Barrington L. Simon, 717 Wooghaven, Ancaster, Ontario (CA) L9G 5B1; Arcady Rozenshteyn, 23824 Glenhill Dr., Cleveland, OH (US) 44122; Gennadii Ivtsenkov, 386 Rexford Drive, Hamilton, Ontario (CA) L8W 3Y7

( * ) Notice: Subject to any disclaimer, the term of this patent is extended or adjusted under 35 U.S.C. 154(b) by 323 days.

(21) Appl. No.: 11/856,771

(22) Filed: Sep. 18, 2007

(65) Prior Publication Data

US 2009/0073538 A1  Mar. 19, 2009

(51) Int. Cl.
*G02F 1/11* (2006.01)
*G02F 1/33* (2006.01)
(52) U.S. Cl. ....................... 359/285; 359/312
(58) Field of Classification Search ........ 359/285, 359/305, 308, 311–312
See application file for complete search history.

(56) References Cited

U.S. PATENT DOCUMENTS

2007/0037332 A1* 2/2007 Tanaka ................. 438/166
2009/0073543 A1* 3/2009 Pannell et al. .......... 359/305

* cited by examiner

*Primary Examiner*—Scott J Sugarman
*Assistant Examiner*—Dawayne A Pinkney

(57) ABSTRACT

Two-coordinate AO laser scanner for 355 and 266-nm UV wavebands utilizing AO cells with specially shaped $TeO_2$ and KDP AO crystals, and equipped with $LiNbO_3$ pulse-fed transducers of special configuration that allows enlarging scanning angle. This technology is utilized in computer-controlled UV laser analyzer of micro-objects, which performs florescent and reflected light analysis of any chosen micro-spot of a sample, and UV laser micro-machining unit that can process a sample with simultaneous control of the operation by built-in CCD camera. The technical solution utilized in the analyzer and micro-machining unit allows precisely matching coordinates of the processed sample and CCD matrix.

4 Claims, 3 Drawing Sheets

ACOUSTO-OPTICAL LASER SCANNER AND UV LASER ANALYZER OF MICRO-OBJECTS BASED ON IT

FIELD OF INVENTION

The present invention relates to technology controlling angular position of coherent UV laser beam. More particularly, the invention pertains to utilize two-coordinate acousto-optical deflectors in laser scanning devices. The present invention, also, relates to research and measurement of physical characteristics of micro-objects and its processing by applied focused laser beam.

BACKGROUND OF THE INVENTION

UV laser radiation is widely utilized now in variety of application fields including biology, chemistry, medicine, micromachining and photolithography. Some of these applications require very precise positioning of the micron-size focused laser beam on a micro-object. Today's commonly used scanning systems utilize electromechanical and mirror-based scanners, such as moving table and galvanometric scanning heads. Such device is described in U.S. Pat. No. 6,057,525 issued May 2, 2000. Here, a laser beam of visible wavelength is scanned by two—X and Y—mirrors angularly turned by electromechanical actuators. According to the patent, such scanning device provides accuracy of 1 microradian in scanning frequency range from 1 Hz to 1,000 Hz.

Such electromechanical scanners have very significant disadvantage, such as low scanning speed and other related to mechanical moving elements (inertia, low lifetime, etc.). Another, not-mechanical scanning method is described in U.S. Pat. No. 5,361,269 issued Nov. 1, 1994. Here, a variable-wavelength laser beam enters a diffraction grating. One-dimensional angular scanning is performed here by changing the laser wavelength that changes diffraction angle. According to the patent, such system provides single axis deflection only. Therefore, to perform two-axis deflection, this scanner has to have additional mechanical scanning device. Such solution, obviously, can not provide fast scanning speed too.

There is another solution, where scanning devices uses two-coordinate acousto-optical (AO) deflector working in UV waveband, such as one described in the article: "Anisotropic Bragg light deflector without midband degeneracy", T. Yano et al. APL v.26, No 12, June 1975. The deflector comprises two $TeO_2$ AO cells that work at 633-nm wavelength. RF signal feeding transducers of AO cells has the range of 38-88 MHz and provides deflection angle of 2.5 arc degrees.

There are some attempts to create AO deflector for UV radiation. To achieve deflection angle of 2 arc degrees these deflectors require higher frequency of RF signal, such as 140-240 MHz. Such high frequency, because of high-frequency acoustic signal absorption, causes overheating problems and requires special low-sickness transducer. Also, $TeO_2$ crystal has to have trapezoidal shape, wherein the angle of input and output window inclination has to be 92.28 and 91.63 arc degrees respectively.

For example, Electro-Optical Products (EOPC), Inc. provides two-coordinate AO scanners DTXY-100, DTXY-250 and DTXY-400 based on $TeO_2$ AO cells. These scanners work at 355-1,600-nm wavelength and provide 2.3-arc degree deflection at 1,064 nm. The efficiency of these deflectors does not exceed 50%.

Another UV scanner—UV266K—produced by EOPC comprises AO cells based on fused silica, which allows working with shorter wavelength (less than 180 nm), but drastically diminish angle of deflection (less than 0.4 arc degrees).

Therefore, higher deflection angles and shorter wavelength require high frequency and power of RF signal feeding the AO cell that cause distortion of deflected laser beam, overheating the crystal and, finally, causes the cell failure.

Thus, described above AO scanners do not allow completely utilizing all advantage of AO technology in UV waveband.

A laser scanner is commonly utilized as a core element of complex devices for scientific research and material processing, such as interactive microscopes and micromachining units. One of such application is a florescent analyzer that receives florescence induced by UV laser beam scanning a sample of biological or chemical substance. Another application of such device is an interactive microscope—the combination of optical microscope and laser scanner built in a single unit, wherein a sample that is visible in optical microscope can be controllably affected by focused laser beam precisely positioned on the sample by the laser scanner. Such device also allows controlling the processing in real time. Because the laser scanner is the main part of such devices, its characteristics determine the characteristics of whole device.

OBJECT OF THE INVENTION

The object of the present invention is to provide two-coordinate AO laser scanner for UV waveband having enlarged scanning angle and minimized power of controlling RF signal.

SUMMARY OF THE INVENTION

The present invention alleviates the disadvantages of the prior art by utilization of an input enlarger-collimator, specially-shaped $TeO_2$ and KDP-based AO cells and special feeding of AO cell by RF signal. Also, the cells design utilizes advanced architecture of the ultrasonic (US) transducers transforming the RF signal into acoustic one.

There are two designs of AO scanners, one for short 266-nm UV and another one—for 355-nm UV.

The 266-nm scanner utilizes set of two AO cells, wherein aperture of the second cell turned against the first one in such a way that provides laser beam deflection in two orthogonal planes. There is variety of cell materials on which the cell can be based—KDP ($KH_2PO_4$), DKDP ($KD_2PO_4$), $NH_4H_2PO_4$, or $RbH_2PO_4$. The transducer transforming PF signal into ultrasonic acoustic wave ($LiNbO_3$ crystal) is positioned on one side of the crystal and absorbent of the acoustic wave—on the opposite side. The crystal is positioned against incoming laser beam in such a way that the acoustic wave propagates across the crystal and the angle between the laser beam and direction of acoustic wave propagation is equal to Bragg angle providing the maximal angle of deflection and maximal efficiency of the deflection. Such specially-shaped crystal equipped with transducer and mounted in frame is AO cell—the main element of any AO scanner. The design of AO cell based on KDP crystal is depicted in FIG. 1.

The crystal of the first cell is positioned in such a way that polarization vector of the laser beam is perpendicular to axis [001] of the crystal. The side of the crystal surface where the transducer is mounted angled about the entering plane (input aperture) on $\alpha_1$ (90-92 arc degrees), about the plane of output aperture—on $\alpha_2$ (90-92 arc degrees) and about the axis [001]—on $\alpha_3$ (1.5-3.5 arc degrees) as depicted on FIG. 1. Such crystal shape allows to output laser beam axis (at central RF frequency) being parallel to incoming beam axis that simplifies design and alignment of the scanner. The second crystal is turned around axis [001] on 90 arc degrees. Such set of the cells provides two-dimensional deflection. In this design, the transducer consists of set of separate 30-microne plates as depicted in FIG. 2. Such design provides uniform acoustic wave in the crystal in RF frequency band of 55-105 MHz. The plates are fixed on one side of each crystal and electrically connected in sequence. Electrical unit developing the RF signal has the triggering input synchronizing laser pulse with the RF pulse feeding the cells.

The features of AO cells allow simultaneously deflecting a laser beam and controlling its intensity. Thus, AO cell works as a modulator too.

The second design of the scanner operating with 355-nm UV utilizes $TeO_2$ crystals that can not be used in 266-nm waveband because of high light absorption at this wavelength, but can successfully work at 355-nm wavelength providing high deflection angle and diffraction efficiency. The design of the scanner is generally similar to design of 266-nm scanner, except the cell material and some distinctions specific for $TeO_2$ crystals. Particularly, side angles $\alpha_1$, $\alpha_2$ and $\alpha_3$ of the crystals are respectively equal to 91-94, 90-93 and 5-7 arc degrees. Such crystal shape allows to output laser beam axis (at central RF frequency) being parallel to incoming beam axis that simplifies design and alignment of the scanner. The design of AO cell based on $TeO_2$ crystal is depicted in FIG. 3. The transducer, unlike to one of the first design, is made of single 13-micron plate of $LiNbO_3$ crystal. The cell operates in 140-240 MHz RF frequency band. Electrical unit developing the RF signal has the triggering input synchronizing laser pulse with the RF pulse feeding the cells. Such pulse feeding of AO cells—the important advantage of the UV scanners of the present invention—significantly diminish the crystal heating. That allows increasing RF frequency and RF signal amplitude so increase deflection angle and efficiency.

DETAILED DESCRIPTION OF THE PREFERRED EMBODIMENTS OF THE INVENTION

266-nm UV Scanner

The scheme of the invention is depicted in FIG. 4. The scanner comprises UV laser 1, changeable collimator 2 with optical axis matched with the axis of input laser beam, AO cells 4 and 5 containing KDP or DKDP crystal, output objective lens 6 and operational field 7, where the deflected laser beam is focused by the objective lens 6. Cells 4 and 5 comprise transducers 8 and 9 firmly mounted on one side of each crystal. Each transducer, 8 and 9, contains a set of thin $LiNbO_3$ plates electrically connected in sequence. On the side of each crystal opposite to one, where the transducer is mounted, a layer of acoustic absorbing resin 13 is applied. The transducer 8 electrically connected to output 1 of electronic unit 11, and the transducer 9 is connected to output 2 of the unit 11. The electronic unit 11 contains two RF generators and controllable amplifiers. The RF pulses developed by the unit 11 feed the transducers 8 and 9 transforming the RF pulses into ultrasonic acoustic wave.

The wave propagates through the cell crystal and produces Bragg diffraction grating deflecting the laser beam passing the crystal. The layer of acoustic absorption resin 13 prevents back reflection of the acoustic wave; therefore, the scanner utilizes the running acoustic wave 12. The position, design and electrical performances of the transducers 8 and 9 allows developing powerful and uniform acoustic wave that increases efficiency of the deflection of two-cell deflector up to 60% at 266-nm wavelength.

The cells of the deflectors are turned about each other in such a way that produces two-dimensional deflection. The AO deflector can simultaneously deflects a laser beam and controls its intensity so working as a modulator too.

The electronic unit 11 has external triggering input/output electrically connected to power supply 19 of the pulse-periodic laser 1 that synchronize pulses of the laser 1 with RF pulses developed by the unit 11. Therefore, RF signal feeds the transducer for about 0.1 milliseconds each time when the laser 1 generates the pulse. This approach allows drastically diminish heat generated by the acoustic wave 12 in the crystal. Because of this, it becomes possible to increase frequency and amplitude of the RF pulse. Thus, the deflection angle increase about twice in comparison with similar AO scanner using continuous feeding; and deflection efficiency increases up to 60% for the set of two cells. This technique is especially applicable for pulse-periodic lasers.

The scanner works as follows:

UV beam 2 of the laser 1 is enlarged by the collimator 3 to fill AO cell's aperture. The enlarged beam enters the AO scanner containing two cells with AO crystals 4 and 5. Electrical RF signals 14 and 15 developed by controlling computer 10 and the electronic unit 11 feed transducers 8 and 9 transforming RF signals 14 and 15 into acoustic wave 12 (cell 4) running at Bragg angle relatively to axis of incoming laser beam. The acoustic wave 12 produces in the crystal body a periodical structure of compression and depression affecting the refraction index of the crystal material creating a sinusoidal phase diffraction grating known as Bragg grating. This kind of diffraction grating theoretically allows efficiently deflecting incoming laser beam in single, the plus first or minus first, diffraction order, wherein the zero order is terminated.

The transducer 8 is mounted on top side of the cell crystal 4, and the transducer 8 is mounted on the left or right side of the cell crystal 5. Therefore, the cell 4 deflects the laser beam in Y, and the cell 5 deflects the beam in X. The laser beam 2 deflected by AO cells 4 and 5 is focused on the operational field 7 (table with sample).

Because of advanced solutions utilized in this embodiment, the scanner of this embodiment provides 0.4 arc degrees of deflection with efficiency more than 60% at 266-nm wavelength.

The crystals that can be utilized in this embodiment, such as KDP ($KH_2PO_4$), DKDP ($KD_2PO_4$), $NH_4H_2PO_4$ and $RbH_2PO_4$, are hygroscopic materials requiring protection coating 16 and 17.

Another Embodiment of the Invention

355-nm UV Scanner

The scheme of the embodiment is depicted in FIG. 5. This embodiment of the invention is generally similar to the previous embodiment, except the cell material and some distinctions specific for $TeO_2$ crystals. Here, the transducers 8 and 9 are the single 13-micron plates of $LiNbO_3$. Such design provides excitation of share acoustic wave in 140-240 MHz RF frequency band. Another difference of this embodiment from the previous one is the shape of the AO crystal. Because of relatively low deflection angle of the scanner of the previous embodiment (0.4 arc degrees), the input and output side of the crystal (KDP) could be parallel to each other. In this particular embodiment, when the deflection angle can reach 2.6 arc degrees, the AO cell crystals 4 and 5 have a prism shape. Here, the input and output sides of the crystals 4 and 5 are slightly inclined that allows the input and deflected beams being parallel to each other at the central frequency of RF signal. Such approach simplifies design and alignment of the scanner.

Because $TeO_2$ crystal is a birefringent one, it transforms incoming linearly polarized light into elliptic one. To convert the polarization back into linear one, the phase shifting plates 4a and 5a are used.

The scanner works as follows:

UV beam 2 of the laser 1 is enlarged by the collimator 3 to fill AO cell's aperture (3-5.5 mm). The enlarged beam passes the phase shifting plate 4a and enters the aperture of the AO cell 4. The beam deflected by the cell 4 passed the phase shifting plate 5a enters the aperture of the AO cell 5. Electrical RF signals 14 and 15 developed by controlling computer 10 and the electronic unit 11 feed transducers 8 and 9 transforming RF signals 14 and 15 into acoustic wave 12 (cell 4) running at Bragg angle relatively to axis of incoming laser beam. The acoustic wave 12 produces in the crystal body Bragg grating.

The transducer 8 is mounted on top side of the cell crystal 4, and the transducer 9 is mounted on the left or right side of the cell crystal 5. Therefore, the cell 4 deflects the laser beam in Y, and the cell 5 deflects the beam in X. The laser beam 2 deflected by AO cells 4 and 5 is focused on the operational field 7 (table with sample). The AO cells 4 and 5 also control laser beam intensity so working as a modulator too.

The electronic unit 11, which contains two RF generators and controllable amplifiers, has external triggering input/output electrically connected to power supply 19 of the pulse-periodic laser 1 that synchronize pulses of the laser 1 with RF pulses developed by the unit 11. Therefore, RF signal feeds the transducer for about 0.1 milliseconds each time when the laser 1 generates the pulse. This approach allows drastically diminishing heat generated by the acoustic wave 12 in the crystal. Because of this, it becomes possible to increase frequency and amplitude of the RF pulse. Thus, the deflection angle increase about twice in comparison with similar AO scanner using continuous feeding; and deflection efficiency increases up to 60% for the set of two cells. This technique is especially applicable for pulse-periodic lasers.

Because of advanced solutions utilized in this embodiment, the scanner of this embodiment provides 2.6 arc degrees of deflection with efficiency more than 60% at 355-nm wavelength.

Another Embodiment of the Invention

UV Laser Analyzer for Researching of Micro-Objects by Means of Applied Laser Radiation This embodiment of the invention is depicted in FIG. 6.

The scanning device of this embodiment utilizes the AO scanners of the previous embodiments depicted in FIG. 4 and FIG. 5.

This embodiment comprises AO laser scanner and two optical receivers. The laser scanner contains UV laser 1 equipped with power supply 2, two-coordinate AO scanner 4 with its electronic controlling unit 5, and objective lens 6 focusing deflected laser beam on the sample 7. Movable table 8 allows positioning the sample 7 in working field of the scanner. Operation of the AO laser scanner is controlled by computer 13.

Sample florescence induced by the laser beam is focused by lens 10 on optical detector 9 equipped with narrow-waveband filter 14 terminating UV light reflected from the sample. The detector 9 is optically connected by computer 13.

UV light reflected from the sample is focused on optical detector 11 equipped with filter 15 terminating florescence of the sample and ambient visible light. The detector 11 is optically connected to computer 13.

Therefore, the scanner programmable positions UV laser beam on the sample, and detectors 9 and 11 receive florescent response and reflected UV light so providing two-channel analysis of irradiated pixel. Because of AO scanner features, it can perform programmable beam scanning, as will as a manual positioning of the laser beam.

Another Embodiment of the Invention

UV Laser Analyzer—Interactive Microscope for Researching of Micro-Objects by Means of Applied Laser Radiation This embodiment of the invention is depicted in FIG. 7.

Here, UV laser analyzer of the previous embodiment additionally equipped with CCD camera 11, wherein CCD matrix coordinates are precisely matched with coordinates of deflected laser beam on the sample 7. Additionally, the optical detector 9—the receiver of florescent response—is equipped with AO filter 10 that allows performing the florescent analysis at different wavelengths.

The analyzer works as follows:

UV laser beam emitted by laser 1 is deflected and modulated by AO scanner 4 that is controlled by electronic unit 5. The deflected laser beam is focused on the sample 7 by objective lens 6. Movable table 8 allows positioning the sample 7 in working field of the scanner. Operation of the AO laser scanner is controlled by computer 13.

To visualize the sample and match the coordinates, the analyzer is equipped with high-resolution CCD camera 11 connected to the computer 13 and micro-objective 12. Lamp 24 illuminates the sample; the reflected light is directed on the CCD camera input by dichroic mirror 23 transparent for UV and reflective for visible light. Therefore, the sample becomes visible on computer monitor 25.

To match coordinates of the focused beam on the sample 7 with coordinates of elements of CCD camera 11 and correct non-linearity of AO scanner, the scanner 4 perform setup scanning controlled by the computer 13, wherein the scanner sequentially positions the beam on a few pixels on the working field of the analyzer. In the setup operation the lamp 24 is switched off, and sample 7 is substituted by thin glass plate with organic dye providing uniform florescent response. CCD camera 11 receives the florescence of irradiated pixels and computer 13 calculates the coordinate of these pixels on CCD matrix and its florescent intensity. According to obtained results the computer 13 performs necessary correction of frequency and amplitude characteristics of the AO scanner 4. In the result, the scanner provides uniform irradiation of each pixel of the working field, the linearity of the working field and matching of the coordinates of working field pixels with elements of CCD matrix.

The receiver of florescent response, the optical detector 9, is equipped with focusing lens 26 and AO filter 10, which allows receiving the florescence of the irradiated pixels in different wavelengths sequentially switched by the filter 10. The filter 10 is controlled by the computer 13.

The analyzer can perform programmable scanning of the sample, as will as a manual positioning of the laser beam. In the manual mode, the operator positions cursor on the processed pixel, switches off the lamp 24 and expose the pixel. The florescent response is received by the receiver 9 and processed by the computer 13. In the programmable scanning mode, the map of processed pixel with its exposure values is loaded in the computer 13 memory. The florescent response of processed pixels is sequentially received by the receiver 9 and further processed by the computer 13.

THE DRAWINGS

Figure 1:
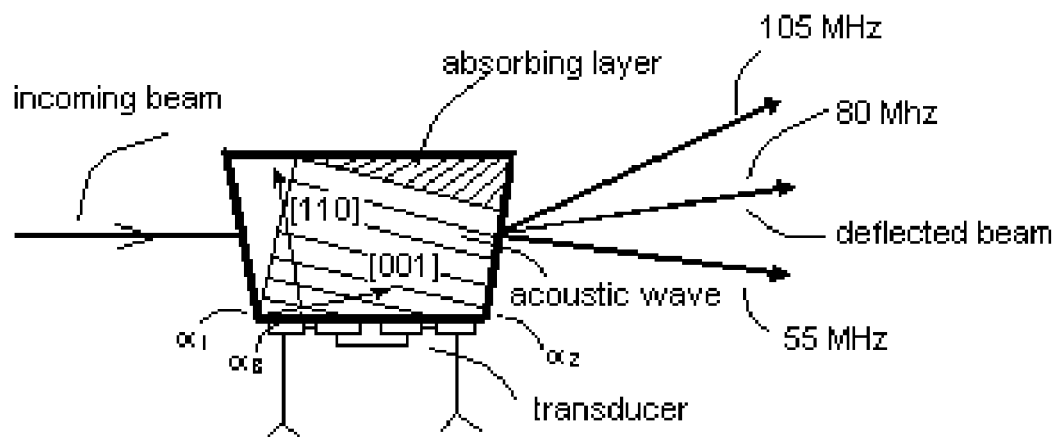
FIG. 1 depicts the design of KDP-based cell specified for 266-nm UV.
Figure 2:
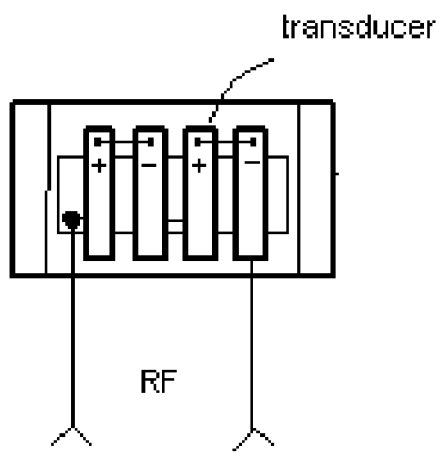
FIG. 2 depicts design of transducer of KDP-based cell specified for 266-nm UV.
Figure 3:
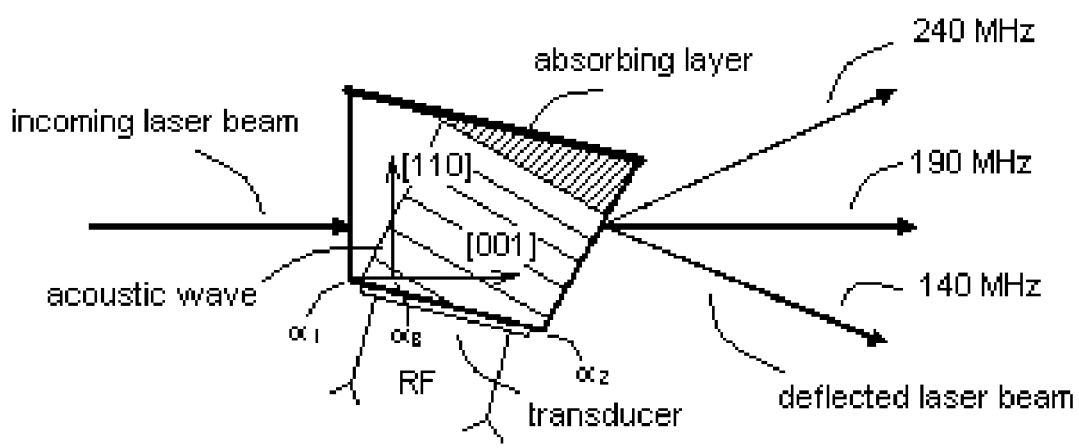
FIG. 3 depicts the design of TeO$_2$-based cell specified for 355-nm UV.
Figure 4:
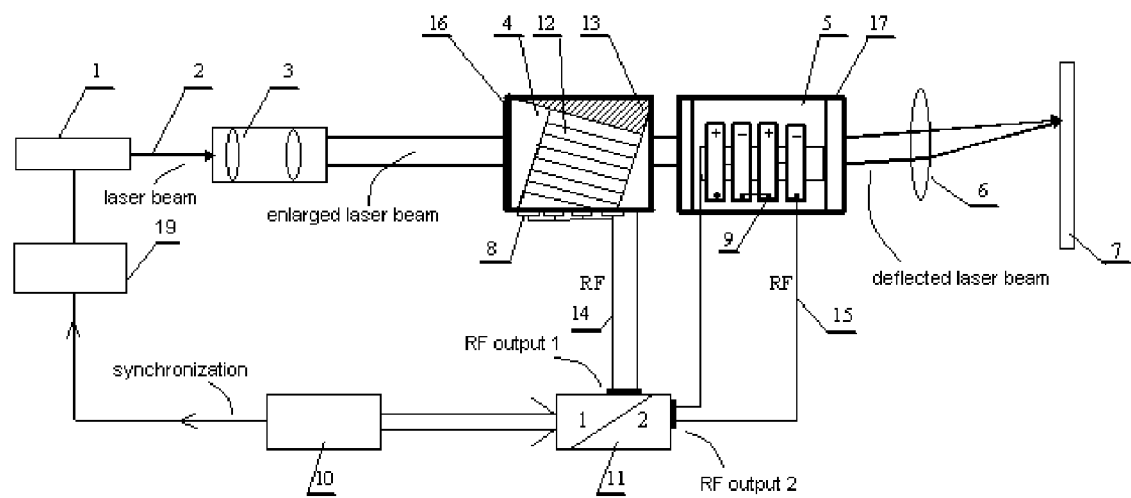

FIG. 4 diagrammatically depicts the object of the invention—266-nm UV SCANNER.

Figure 5:
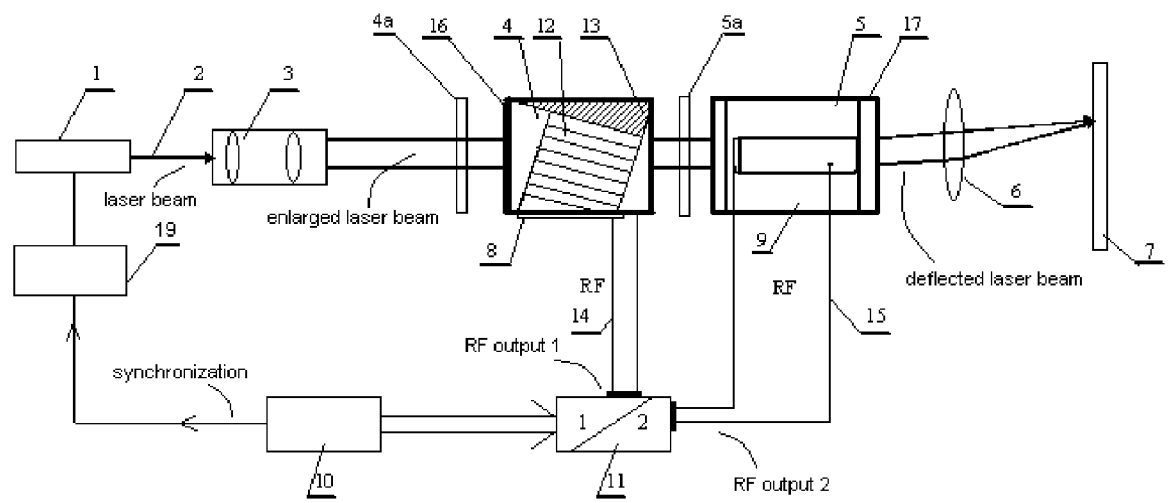

FIG. 5 diagrammatically depicts the object of the invention—355-nm UV SCANNER.

Figure 6:
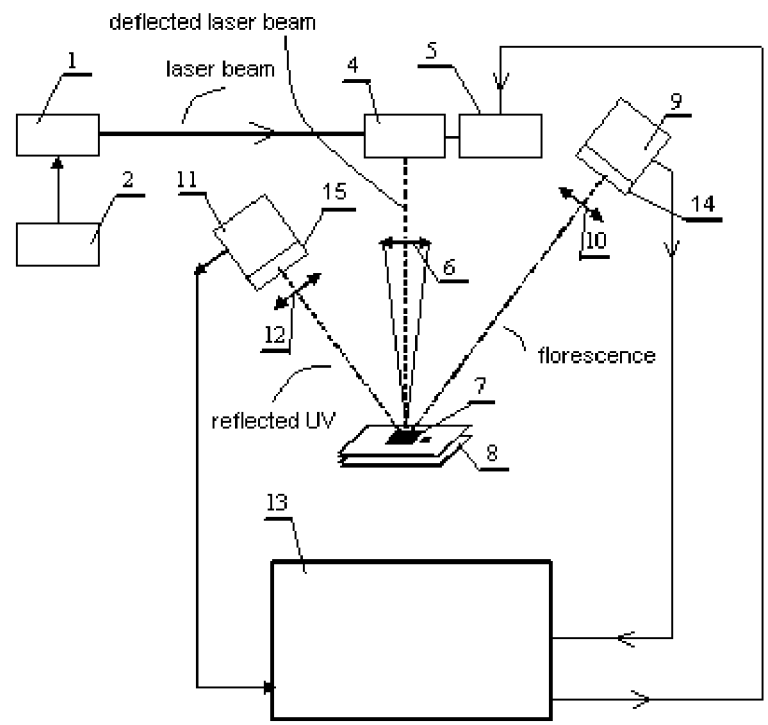

FIG. 6 diagrammatically depicts the object of the invention—UV laser analyzer for researching of micro-objects.

Figure 7:
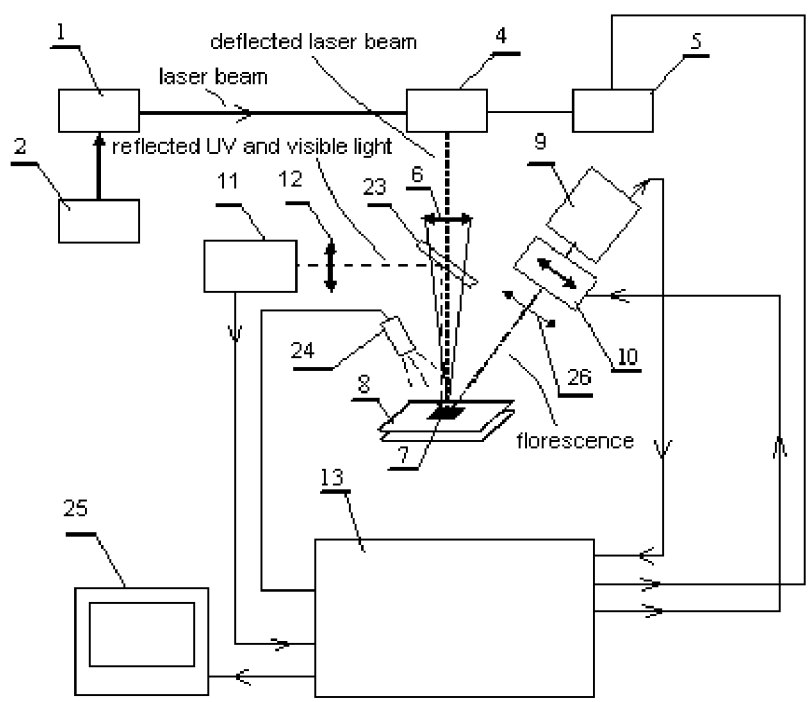

FIG. 7 diagrammatically depicts the object of the invention—UV laser analyzer—interactive microscope for researching of micro-objects.

What is claimed is:

1. Two-coordinate acousto-optical UV laser scanner comprising:
    a. a collimator having optical axes aligned with the axis of incoming UV laser beam;
    b. a first and a second identical crystals that are transparent for UV radiation, wherein said second crystal is turned around axis of said laser beam on 90 arc degrees;
    c. a transducer transforming electrical RF signals into acoustic ones, wherein said transducer is positioned on one side of each said crystal in such a way that acoustic wave is propagate in each said crystal at Bragg angle;
    d. a resin layer absorbing said acoustic wave, wherein said layer is positioned on one side of each said crystal that is opposite to side where said transducer is positioned;
    e. a first electronic unit programmable developing said RF signals feeding said transducer of said first crystal, wherein output of said unit is in electrical connection with said transducer of said first crystal;
    f. a second electronic unit programmable developing said RF signals feeding said transducer of said second crystal, wherein output of said unit is in electrical connection with said transducer of said second crystal;
wherein the improvement comprises:
    said first and said second crystal being made of KDP (KH$_2$PO$_4$), or DKDP (KD$_2$PO$_4$), or NH$_4$H$_2$PO$_4$, or RbH$_2$PO$_4$, wherein frontal side of said crystal is positioned perpendicularly to said incoming laser beam, axis of said crystal is in perpendicular to polarization vector of said incoming laser beam, and side of said crystal with said transducer is positioned at 1.5-3.5 arc degrees to axis of said crystal, whereas said second crystal that is identical to said first crystal is turned around axis of said incoming laser beam at 90 arc degrees;
    said transducer comprising two and more 30-micron plates of LiNbO$_3$, wherein said plates are firmly fastened on one side of said crystal in sequences and electrically connected in sequences;
    said electronic units having external triggering inputs, which allow synchronizing pulses of said laser with said RF signals feeding said transducers so providing pulse feeding of said transducers.

2. Two-coordinate acousto-optical UV laser scanner of claim 1, wherein the crystal of claim 1 made of TeO$_2$ in prism shape with side angled relatively axis of said crystal at angles $\alpha_1$, $\alpha_2$ and $\alpha_3$, and additionally comprising:
    a phase-shifting plate installed in the front of said crystal and transforming linearly-polarized laser beam of claim 1 into elliptically-polarized one propagating along axis of said crystal:
    said LiNbO$_3$ transducer made as single 13-micron plate firmly fastened on one side of each said crystal that allows working in 140-240 MHz frequency band.

3. UV laser analyzer of micro-objects by means of applied laser radiation comprising:
    a UV laser with power supply;
    a collimator enlarging incoming laser beam;
    a laser beam modulator;
    a two-coordinate laser scanner;
    an objective lens focusing deflected laser beam on a sample;
    a movable table, on which said sample is placed;
    a receiver of florescent light induced in said sample by said UV laser beam;
    a receiver of UV light reflected from said sample irradiated by said UV laser beam;
    a computer with software controlling said analyzer;
wherein the improvement comprises:
    the two-coordinate laser scanner of claim 1;
    said receiver of florescent light equipped with a narrow-waveband filter terminating UV light reflected from said sample and ambient light;
    said receiver UV light reflected from said sample equipped with a filter terminating florescence of the sample and ambient visible light.

4. The UV laser analyzer of claim 3 further comprising:
    a CCD camera being in electrical communication with the computer of claim 3
    a micro-objective of said CCD camera;
    a dichroic mirror transparent for UV laser beam, which reflects image of illuminated said sample and florescence of said sample irradiated by UV laser beam on CCD camera input;
    the software of claim 3 comparing coordinates of pixels on said sample with coordinates of elements of matrix of said CCD camera to develop amplitude and frequency correction of the two-coordinate laser scanner of claim 3;
    the receiver of florescent light of claim 3 equipped with acousto-optical filter being controlled by said computer, which allows performing florescent analysis in different wavelengths.

\* \* \* \* \*